US006777560B2

(12) United States Patent
Nelson et al.

(10) Patent No.: US 6,777,560 B2
(45) Date of Patent: Aug. 17, 2004

(54) PROCESS FOR PREPARING 5-(4-FLUOROPHENYL)-1-[2-((2R,4R)-4-HYDROXY-6-OXO-TETRAHYDRO-PYRAN-2-YL)ETHYL]-2-ISOPROPYL-4-PHENYL-1H-PYRROLE-3-CARBOXYLIC ACID PHENYLAMIDE

(75) Inventors: Jade D. Nelson, Holland, MI (US); Michael G. Pamment, Holland, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/635,317

(22) Filed: Aug. 6, 2003

(65) Prior Publication Data

US 2004/0068121 A1 Apr. 8, 2004

Related U.S. Application Data

(60) Provisional application No. 60/401,707, filed on Aug. 6, 2002.

(51) Int. Cl.[7] .................................. C07D 407/06
(52) U.S. Cl. ............................................ 548/517
(58) Field of Search ........................................ 548/517

(56) References Cited

U.S. PATENT DOCUMENTS

| 4,681,893 A | 7/1987 | Roth et al. |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth et al. |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,969,156 A | 10/1999 | Briggs et al. |
| 5,998,633 A | 12/1999 | Jacks et al. |
| 6,087,511 A | 7/2000 | Lin et al. |
| 6,121,461 A | 9/2000 | McKenzie |
| 6,476,235 B2 | 11/2002 | Butler et al. |

OTHER PUBLICATIONS

Saburi et al., Asymmetric Hydrogenation of 3,5–Dioxoesters Catalyzed by Ru–binap Complex: A Short Step Asymmetric Synthesis of 6–Substituted 5,6–dugydro–2–pyrones, Tetahedron, vol. 49(10): 1997–2010 (1993).

Carpentier, et al., One–Pot and Sequential Asymmetric Hydrogenation of b, o–Diketoesters into Functionalized 1,3–Diols: From anti– to syn–Steroselectivity, Eur. J. Org. Chem, 3421–3427 (1999).

Noyori, et al., Asymmetric Transfer Hydrogenation Catalyzed by Chiral Ruthenium Complexes, Acc. Chem. Res., 30(2): 97–102 (1997).

Palmer et al., Asymmetric transfer hydrogenation of C=O and C=N bonds, Tetrahedron: Asymmetry, 10(11): 2045–2061 (1999).

Primary Examiner—Ceila Chang
Assistant Examiner—Sonya Wright
(74) Attorney, Agent, or Firm—Heidi M. Berven

(57) ABSTRACT

A method for preparing 5-(4-fluorophenyl)-1-[2-((2R,4R)4-hydroxy-6-oxo-tetrahydro-pyran-2-yl)-ethyl]-2-isopropyl-4-phenyl-1H-pyrrole-3-carboxylic acid phenylamide (I), a key intermediate in the synthesis of atorvastatin calcium, is described.

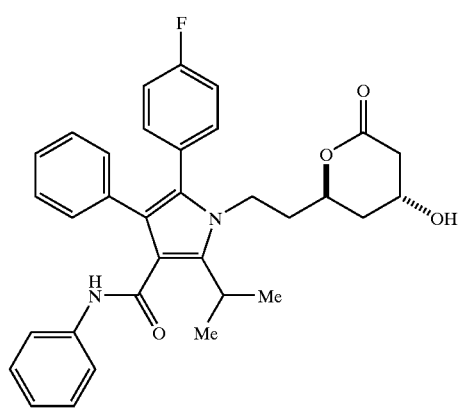

27 Claims, No Drawings

PROCESS FOR PREPARING 5-(4-FLUOROPHENYL)-1-[2-((2R,4R)-4-HYDROXY-6-OXO-TETRAHYDRO-PYRAN-2-YL)ETHYL]-2-ISOPROPYL-4-PHENYL-1H-PYRROLE-3-CARBOXYLIC ACID PHENYLAMIDE

CROSS REFERENCE TO RELATED APPLICATIONS

This application claims benefit of priority from U.S. Provisional Application No. 60/401,707 filed on Aug. 6, 2002.

FIELD OF THE INVENTION

A method for preparing 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide, a key intermediate in the synthesis of atorvastatin calcium, is described.

BACKGROUND OF THE INVENTION 5-(4-Fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide (I) is a key intermediate in the synthesis of atorvastatin calcium (Lipitor®), known also by the chemical name [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate. Atorvastatin calcium inhibits 3-hydroxy-3-methylglutaryl-coenzyme A reductase (HMG-CoA reductase) and thus is useful as a hypolipidemic and/or hypocholesterolemic agent.

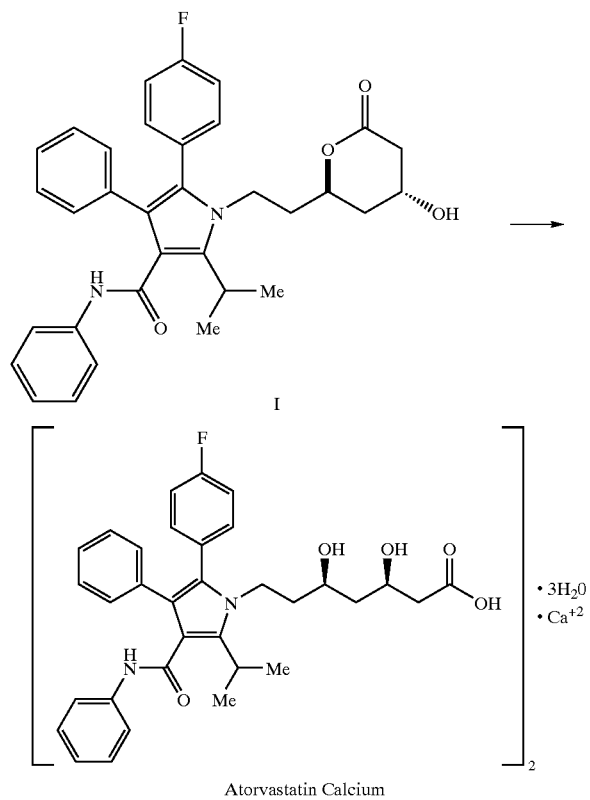

Atorvastatin Calcium

A number of patents have issued disclosing atorvastatin, as well as processes and key intermediates for preparing atorvastatin. These include: U.S. Pat. Nos. 4,681,893, 5,273,995, 5,003,080; 5,097,045, 5,103,024, 5,124,482, 5,149,837, 5,155,251, 5,216,174, 5,245,047, 5,248,793, 5,280,126, 5,397,792, 5,342,952, 5,298,627, 5,446,054, 5,470,981, 5,489,690, 5,489,691, 5,510,488, 5,998,633, 6,087,511, 5,969,156, 6,121,461, 5,273,995 6,476,235, 5,969,156, and 6,121,461.

Existing approaches to the preparation of key intermediate (I) presented some shortcomings. For example, one approach relied on the use of a costly chiral raw material ((R)-4-cyano-3-hydroxy-butyric acid ethyl ester), and a low temperature diastereoselective borane reduction.

Scheme 1 summarizes an alternative approach disclosed in U.S. Pat. No. 6,476,235. Hydrogenation of β,δ diketoacid 2 in the presence of a chiral ruthenium catalyst under acidic conditions proceeded to give diol 3 in moderate to good yields and 1:1 syn:anti diastereoselectivity with respect to the C-3 and C-5 chiral centers. A number of additional transformations are then necessary to reset the stereochemistry of the C-3 center in diol 3 to provide key intermediate (I). These steps include: (a) intramolecular cyclization of 3 to provide lactone 4; (b) elimination of water from lactone 4 to provide α,β unsaturated lactone 5; (c) facial selective Michael addition of allyl or benzyl alcohol to α,β unsaturated lactone 5 to provide saturated lactone 6; and removal of the allyl or benzyl moiety in lactone 6 via hydrogenolysis provided key intermediate (I).

Scheme 1

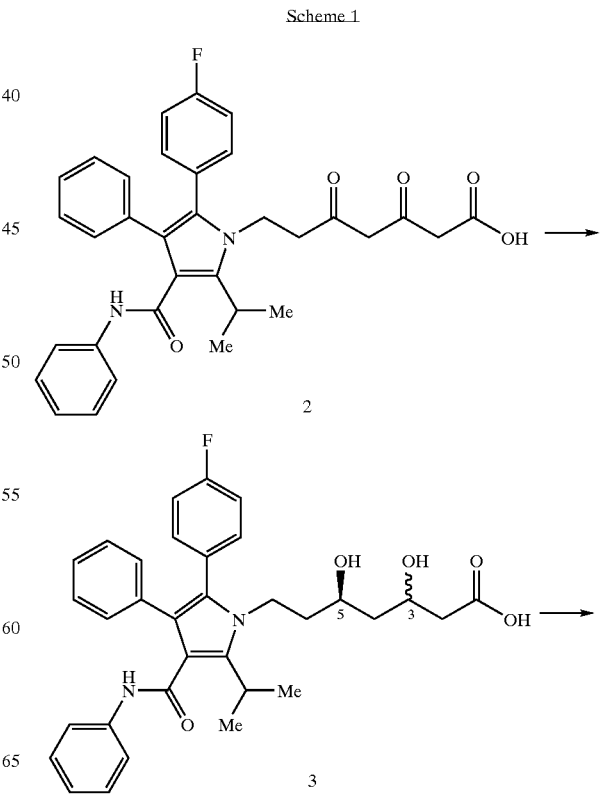

-continued

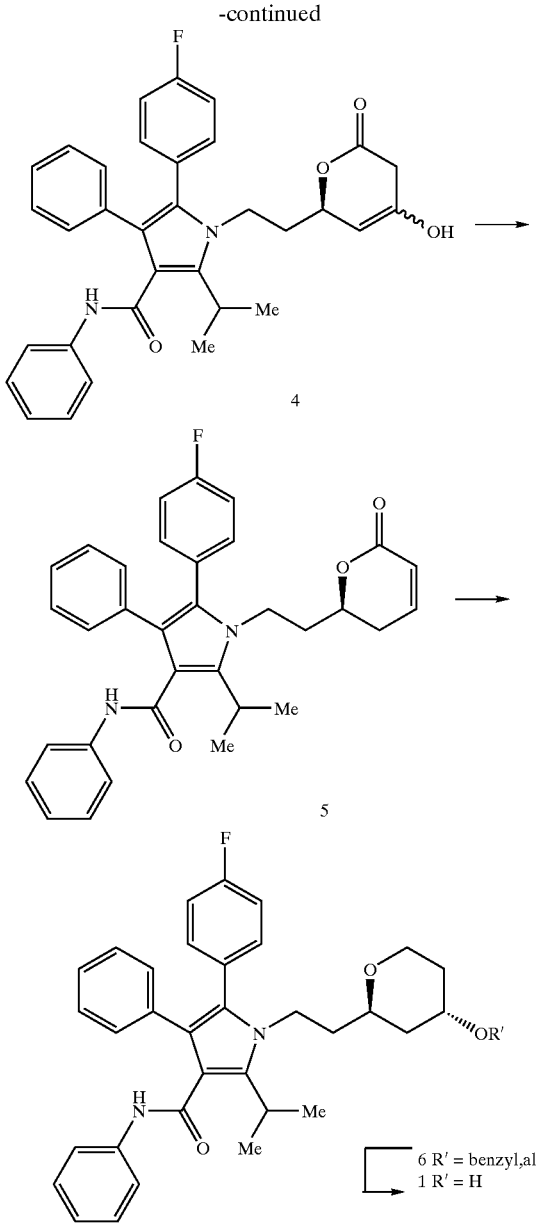

4

5

As a preliminary matter, the asymmetric hydrogenation of ketones is a known transformation in organic synthesis. However, the complexity of the reaction increases in the case of 1,3,5-tricarbonyl systems, and poor yields and poor stereoselectivities often result. In fact, investigations by Saburi (*Tetrahedron*, 1997, 1993;49) and Carpentier (*Eur. J. Org. Chem.* 1999;3421) have independently demonstrated low to moderate diastereo- and/or enantio-selectivities for diketoester asymmetric hydrogenations.

Furthermore, the fact that the processes disclosed in the literature require high pressure hydrogenation and extended reaction times makes the procedures generally impractical and not amenable to large-scale manufacturing processes where safety, efficiency, and cost are critical considerations.

As a result, a need remains for an approach to the preparation of key intermediate (I) that is efficient, inexpensive, proceeds in a minimum of transformations, and occurs in good yield and high levels of diastereoselectivity.

SUMMARY OF THE INVENTION

These and other needs are met by the present invention which is directed to a process for the preparation of a compound of formula (I)

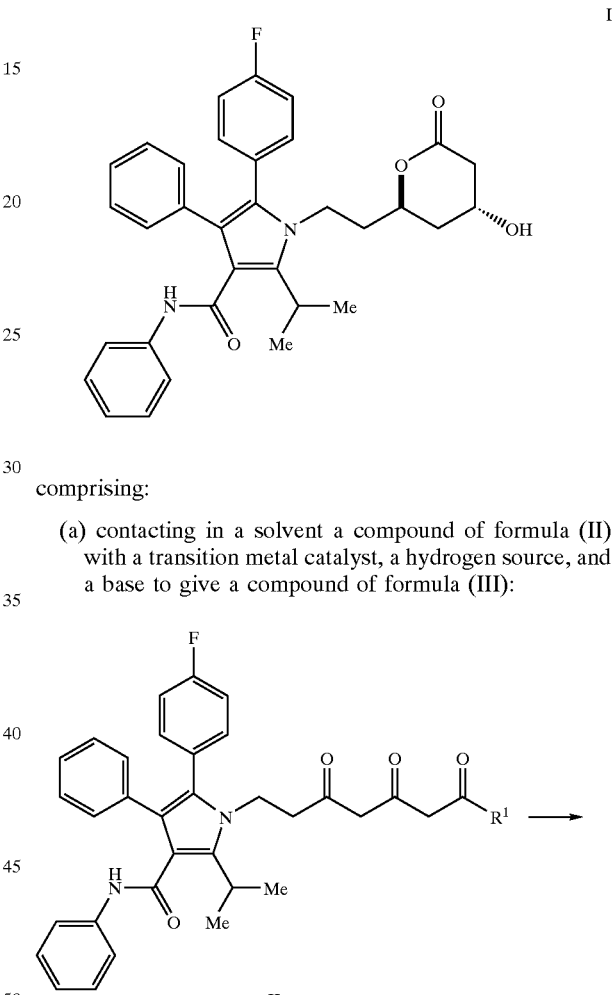

comprising:

(a) contacting in a solvent a compound of formula (II) with a transition metal catalyst, a hydrogen source, and a base to give a compound of formula (III):

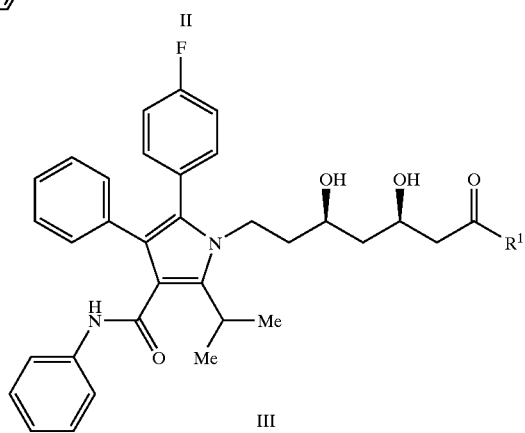

wherein
R¹ is defined as —XR, wherein X is O, S, or Se, or

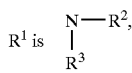

wherein R² and R³ are independently alkyl,
cycloalkyl,
arylalkyl, or
aryl, or
R² and R³ taken together are —(CH₂)₄—,
—(CH₂)₅—,
—(CH(R⁴)—CH₂)₃—,
—(CH(R⁴)—CH₂)₄—,
—(CH(R⁴)—(CH₂)₂—CH(R⁴))—,
—(CH(R⁴)—(CH₂)₃—CH(R⁴))—,
—CH₂—CH₂-A-CH₂—CH₂—,
—CH(R⁴)—CH₂-A-CH₂CH₂—,
—CH(R⁴)—CH₂-A-CH₂—CH(R⁴)—, wherein
R⁴ is alkyl of from one to four carbon atoms,
A is O, S, or NH or NR wherein R is defined
as alkyl, aryl, arylalkyl, or heteroaryl;
(b) conversion of the compound of formula (III) wherein
R¹ is as defined above to a compound of formula (IV)
using base;

and (c) contacting in a solvent the compound of formula (IV)
with an acid to afford a compound of Formula (I).

The invention also provides a process for the preparation
of a compound of formula (I)

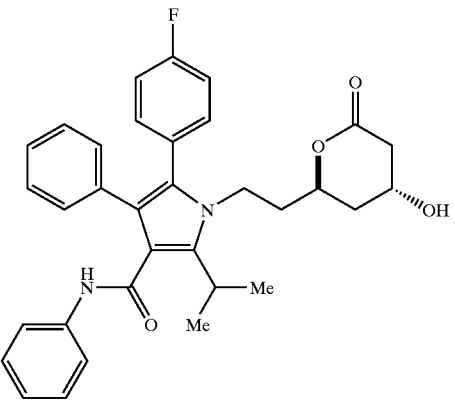

comprising:

(a) contacting in a solvent compound of formula (V) with
a transition metal catalyst, a hydrogen source, and a
base to give a compound of formula (VI):

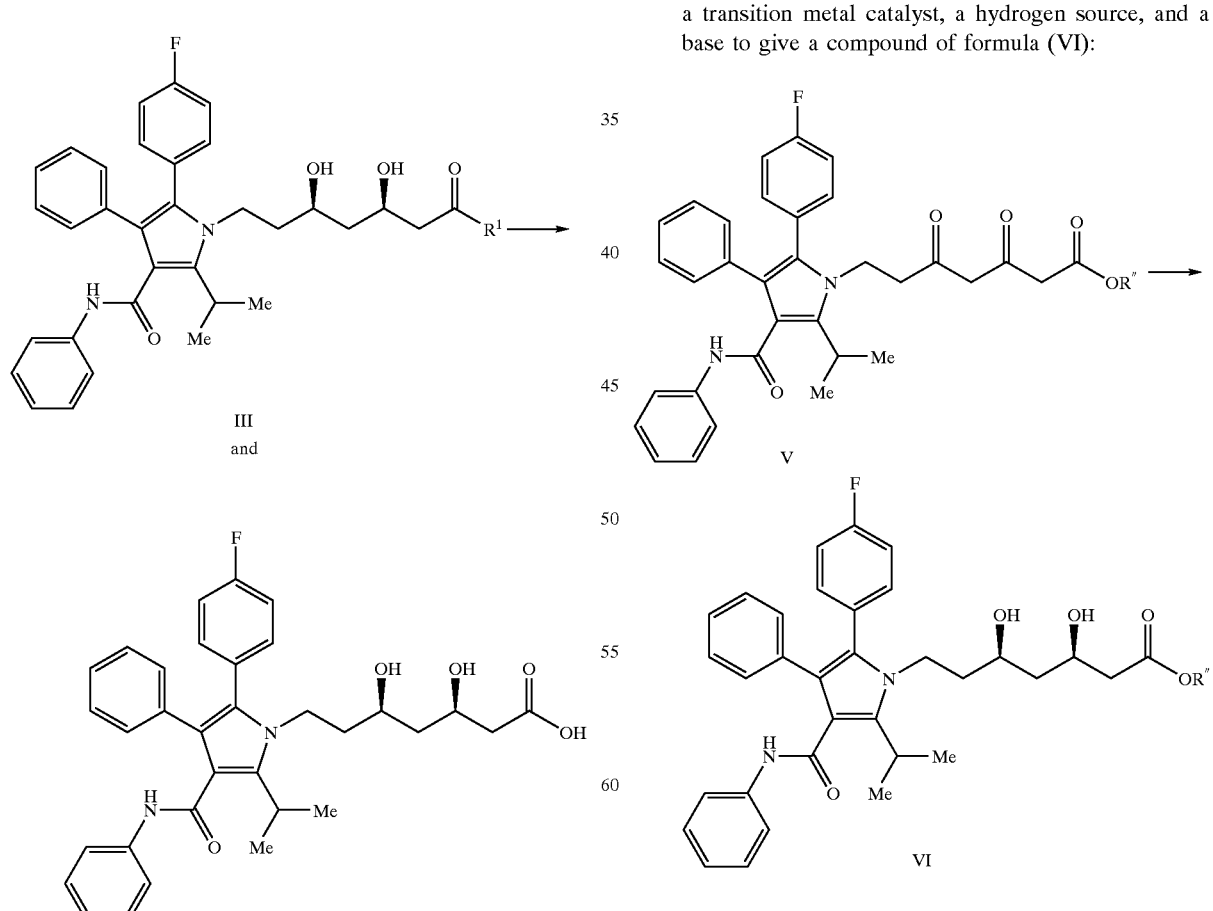

wherein
R″ is defined as Me, Et, or t-Bu;

(b) conversion of the compound of formula (VI) wherein R" is as defined above to a compound of formula (IV) using base;

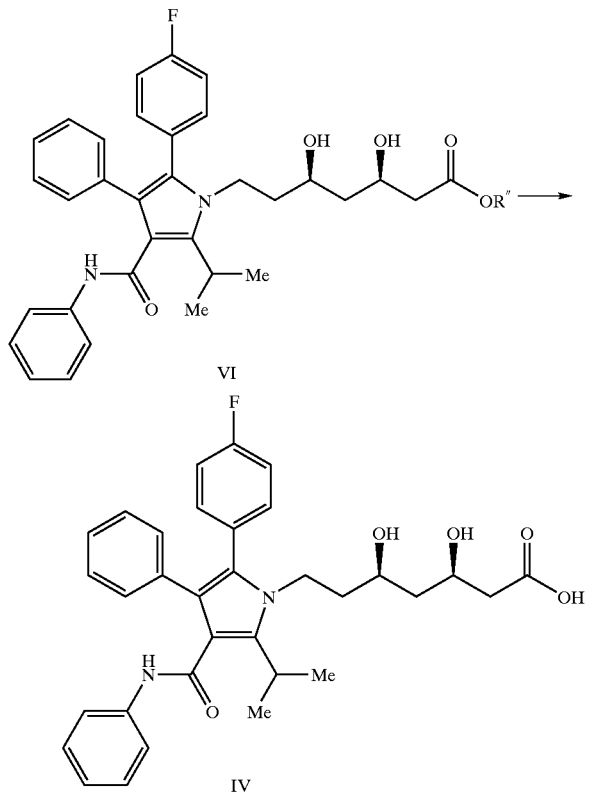

and (c) contacting in a solvent the compound of formula (IV) with an acid to afford a compound of Formula (I).

As disclosed herein, we surprisingly and unexpectedly found that the diol esters of the present invention, (R)-7-[2-(4-fluorophenyl)-5-isopropyl-3-phenyl-4-phenylcarbamoyl-pyrrol-1-yl]-3,5-dihydroxy-heptanoic acid esters, can be obtained directly from the corresponding 1,3,5-tricarbonyl precursors in a highly stereoselective manner via a mild and efficient ruthenium-catalyzed asymmetric transfer hydrogenation reaction utilizing transition metal catalysts with chiral non-racemic ligands. The reaction proceeds in good yields at ambient temperature and atmospheric pressure. The invention process is thus safer and more efficient in large scale than earlier approaches, because it avoids the need for specialized high pressure equipment and the use of hydrogen gas. Because the transfer hydrogenation reaction occurs with high levels of syn diastereoselectivity, additional transformations are not necessary to correct the stereochemistry of the C-3 center, as in previous approaches, and the overall number of steps needed to convert the compound of formula (II) to key intermediate (I) is minimized. Moreover, the invention process avoids the use of a costly, chiral raw material ((R)-4-cyano-3-hydroxy-butyric acid ethyl ester), and a low temperature diastereoselective borane reduction, as was necessary in earlier approaches to the preparation of key intermediate (I).

DETAILED DESCRIPTION OF THE INVENTION

Definitions

The term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a phenylalkyl group, a phenyl group substituted by 1 to 4 substituents selected from alkyl as defined above, alkoxy as defined above, thioalkoxy as defined above, halogen, trifluoromethyl, dialkylamino as defined above for alkyl, nitro, cyano,

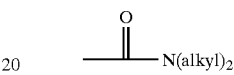

as defined above for alkyl, —$(CH_2)_{n_2}$—$N(alkyl)_2$ wherein $n_2$ is an integer of from 1 to 5 and alkyl is as defined above and

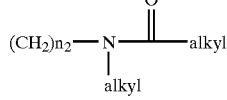

as defined above for alkyl and $n_2$.

The term "heteroaryl" means a 5- and 6-membered heteroaromatic radical which may optionally be fused to a benzene ring containing 1 to 3 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl and the like optionally substituted by a substituent selected from alkyl as defined above, alkoxy as defined above, thioalkoxy as defined above, halogen, trifluoromethyl, dialkylamino as defined above for alkyl, nitro, cyano,

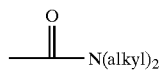

as defined above for alkyl, —$(CH_2)n_2$—$N(alkyl)_2$ wherein $n_2$ is an integer of 1 to 5, and alkyl is as defined above, and as

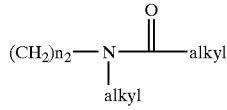

as defined above for alkyl and $n_2$.

The term "arylalkyl" means an aromatic radical attached to an alkyl radical wherein aryl and alkyl are as defined above for example, benzyl, phenylethyl, 3-phenylpropyl, (4-chlorophenyl)methyl, and the like.

Description of Invention Process

The invention process disclosed herein is depicted in Scheme 2 and commences in step (a) with transfer hydrogenation of a compound of formula (II) to form a compound of formula (III). In step (b), the

moiety (typically, an ester or an amide) in the compound of formula (III) is hydrolyzed to form the acid (IV). Finally, in step (c), lactonization of the acid (IV) provides key intermediate (I).

Scheme 2

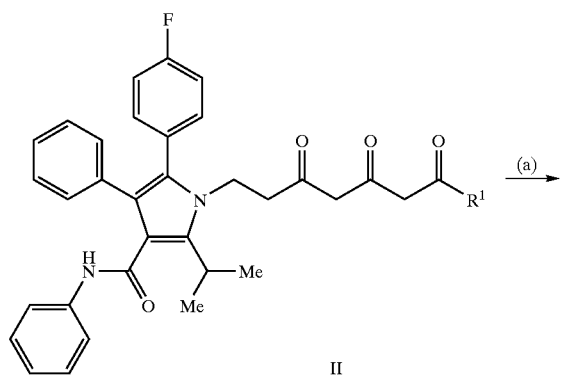

II

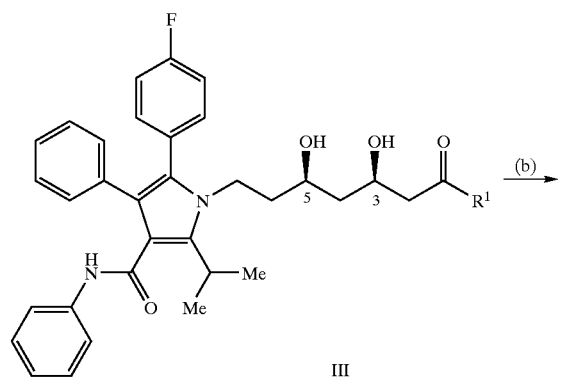

III

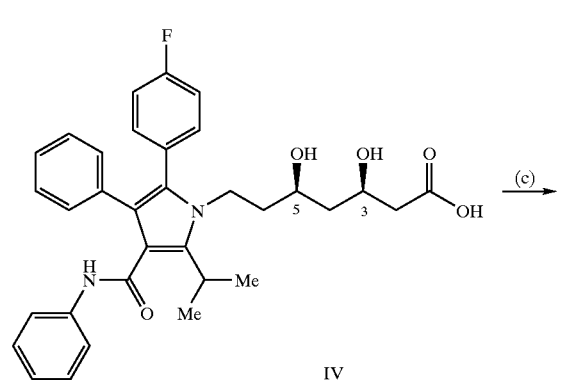

IV

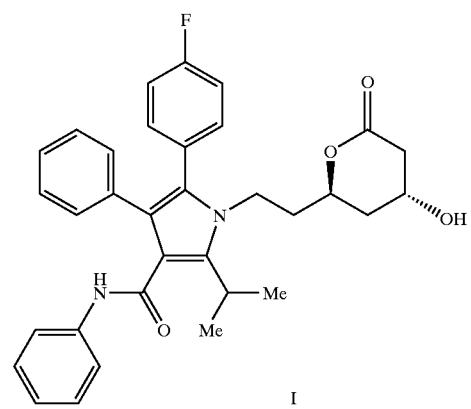

I

As a preliminary note, the carbonyl groups in the compound of formula (II) are shown in the keto form in Scheme 2. However, a compound of formula (II) can undergo "keto-enol" tautomerism and thus can exist in several tautomeric forms (II, II-a, II-b, II-c, and II-d), shown below, all of which are encompassed by the present invention.

II

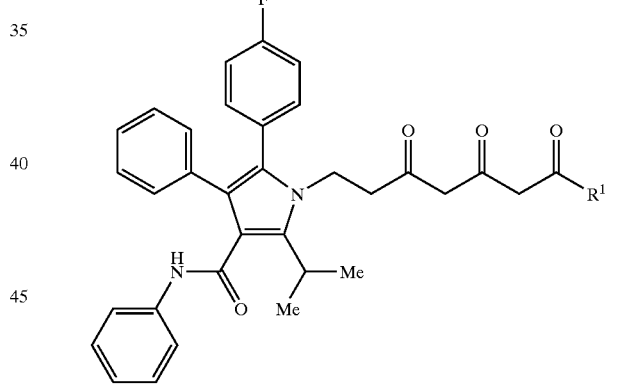

II-a

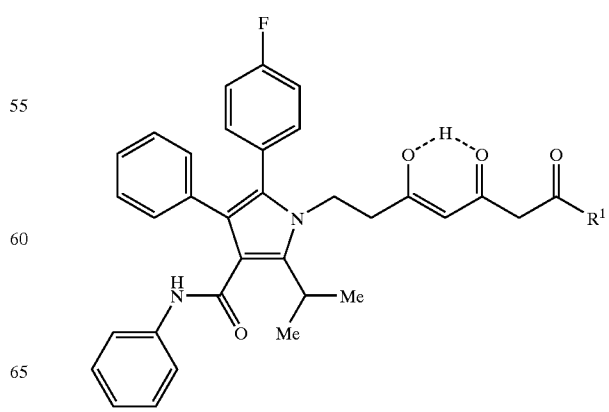

-continued

II-b

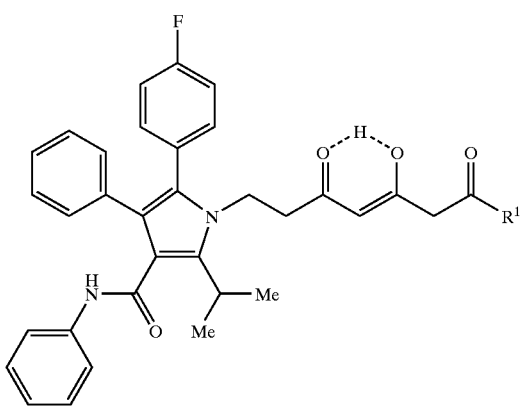

II-c

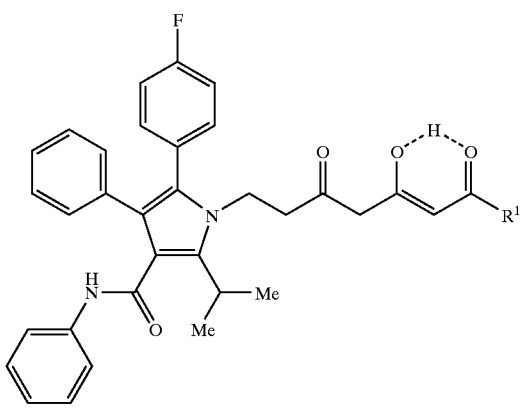

II-d

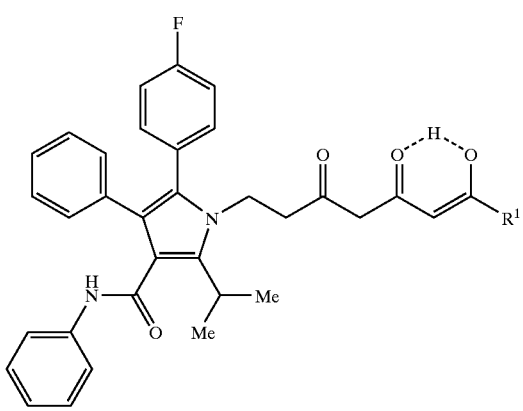

Step (a)

The invention process commences with the transfer hydrogenation of a compound of formula (II) to provide a compound of formula (III). In one embodiment, $R^1$ in a compound of formula (II) is defined as —XR, wherein X is O, S, or Se, or $R^1$ is 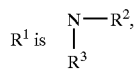

wherein $R^2$ and $R^3$ are independently alkyl,
cycloalkyl,
arylalkyl, or
aryl, or $R^2$ and $R^3$ taken together are —(CH$_2$)$_4$—,
—(CH$_2$)$_5$—,
—(CH(R$^4$)—CH$_2$)$_3$—,
—(CH(R$^4$)—CH$_2$)$_4$—,
—(CH(R$^4$)—(CH$_2$)$_2$—CH(R$^4$))—,
—(CH(R$^4$)—(CH$_2$)$_3$—CH(R$^4$))—,
—CH$_2$—CH$_2$-A-CH$_2$—CH$_2$—,
—CH(R$^4$)—CH$_2$-A-CH$_2$CH$_2$—,
—CH(R$^4$)—CH$_2$-A-CH$_2$—CH(R$^4$)—, wherein $R^4$ is alkyl of from one to four carbon atoms, A is O, S, or NH or NR wherein R is defined as alkyl, aryl, arylalkyl, or heteroaryl.

In another embodiment of the present invention, $R^1$ in a compound of formula (II) is OMe, OEt, or OtBu.

In step (a) of Scheme 2, the compound of formula (II) is contacted with a catalyst such as, for example, a transition metal catalyst with chiral non-racemic ligands in the presence of a hydrogen source and a base. "Contacting" in step (a) comprises mixing the compound of formula II, formic acid, base, and a transition metal catalyst in a solvent to form a homogeneous or heterogeneous mixture.

The solvent in step (a) is typically an anhydrous or aqueous polar aprotic, polar protic, or nonpolar solvent, a ketone, toluene, benzene, or another aryl solvent available to the skilled artisan, or hexane. Thus, the solvent in step (a) is acetonitrile, ethyl acetate, tetrahydrofuran, dimethyl formamide, diethyl ether, methylene chloride, chloroform, methanol, ethanol, isopropanol, toluene, or the like, or mixtures or combinations thereof in the presence or absence of water as a cosolvent.

The concentration of the compound of formula (II) in the solvent in step (a) is generally about 0.2 Molar to about 0.6 Molar. Typically, the concentration is about 0.3 Molar to about 0.5 Molar, and preferably, about 0.35 Molar to about 0.45 Molar.

The transition metal catalyst in step (a) is typically a chiral, non-racemic transition metal catalyst. "Transition metal catalyst" means a catalyst derived from one of the transition metal elements as provided in Rows 1B–8B of the periodic table of the elements. The chiral, non-racemic transition metal catalyst contemplated for use in the invention process include catalysts derived from the elements ruthenium, rhodium, iridium, or the like.

The chiral, non-racemic transition metal catalyst is prepared by reacting a catalyst precursor with a chiral, non-racemic ligand in a solvent such as, for example, methanol, ethanol, isopropanol, or the like, optionally in the presence of a co-solvent, for example, dichloromethane, tetrahydrofuran, toluene or the like, and a base such as triethylamine, according to methods available to the skilled artisan.

Catalyst precursors contemplated for use in the invention process include [dichloro-(1,5-cycloocta-diene)]ruthenium (II) oligomer, [RuCl$_2$benzene]$_2$, [RuCl$_2$p-cymene]$_2$, [RuCl$_2$ mesitylene]$_2$, [dibromo-(1,5-cyclooctadiene)]ruthenium (II) dimer, [bis-(2-methallyl)cycloocta-1,5-diene]ruthenium (II) complex, pentamethylcyclopenta-dienyl iridium (III) chloride dimer, and pentamethylcyclopentadienyl rhodium (III)chloride dimer.

Chiral, non racemic ligands contemplated for use in the invention process include chiral, non-racemic diphosphine ligands as well as chiral diamine ligands. Such ligands are disclosed, for instance, by Noyori, Ryoji; Hashiguchi, and Shohei in Acc. Chem. Res. (1997), 30(2), 97–102; or by Palmer, Matthew J. and Wills, Martin in Tetrahedron: Asymmetry (1999), 10(11), 2045–2061. For example, chiral diamine ligands, chiral amino alcohol ligands can be used to prepare the chiral, non-racemic transition metal catalyst. Chiral diamine ligands include compounds 7 and 8. Chiral alcohol amine ligands include norephedrine and the like.

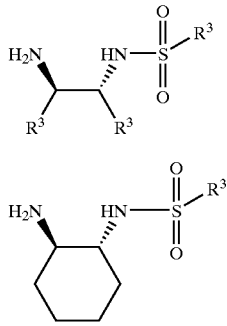

$R^3$ = Alkyl, heteroaryl, or aryl

However, any rhodium, iridium, or ruthenium (II) precursor/diphosphine or /diamine ligand combination may be employed in the transfer hydrogenation reaction of step (a).

Once prepared, the chiral, non-racemic transition metal catalyst is added to a mixture comprising the compound of formula (II), the hydrogen source, base, and solvent. The hydrogen source contemplated for use in the invention process is selected from isopropanol, formic acid, or ammonium formate. If isopropanol is selected as the hydrogen source, it is typically present in large excess and is used with NaOH as the base. If formic acid is selected as the hydrogen source, an amine is selected as the base. If ammonium formate is selected as the hydrogen transfer agent, an excess of ammonia may be used, or just 2 equivalents of a base as described herein may be used. Typically, the hydrogen source employed in step (a) in the invention process is formic acid.

As indicated previously, when formic acid is selected as the hydrogen source, an amine is typically selected as the base for the transfer hydrogenation reaction of step (a). The amine base is typically selected from triethylamine, trimethylamine, ethyldimethylamine, tri-n-propylamine, diisopropylethylamine, 1,8-diazabicyclo[5.4.0.]undec-7-ene (DBU), lutidine, collidine, 4-dimethyl aminomethyl pyridine, diisopropyl amine, piperidine, pyrrolidine, tri-n-butyl amine, 4-methylmorpholine, and the like. Typically, however, the amine base is triethylamine.

In step (a) of the invention process, the molar equivalents of the compound of formula (II), of the hydrogen source, the base, and the transition metal catalyst respectively are generally about 1 equivalent of the compound of formula (II); about 2.0 to about 2.5 equivalents of hydrogen source; about 4 to about 5 equivalents of amine base; and about 0.05 to about 2 mol percent of the transition metal catalyst.

Typically, in step (a) of the invention process, the molar equivalents of the compound of formula (II), of the hydrogen source, the base, and the transition metal catalyst, respectively, are about 1 equivalent of the compound of formula (II); about 2.1 equivalents of hydrogen source; about 4.1 equivalents of amine base; and about 1 mol percent of the transition metal catalyst.

The step (a) mixture comprising the compound of formula (II), chiral, non-racemic transition metal catalyst, hydrogen source, base, and solvent is agitated, for example by employing a mechanical stirrer, magnetic stirrer, or other agitating means available to the skilled artisan, at a temperature of about 0 to about 50° C. Typically, the temperature is about 10 to about 40° C. Preferably, the temperature is about 20 to about 30° C.

The pressure in step (a) is generally atmospheric pressure, or about 0.9 to about 1.1 atmospheres. Typically, the pressure is about 0.95 to about 1.05 atmospheres. Preferably, the pressure is about 0.99 to about 1.02 atmospheres.

The step (a) mixture is typically stirred or otherwise agitated at the temperature and pressure provided above until the reaction is complete by thin layer chromatography, or any other appropriate monitoring method available to the skilled artisan. Generally reaction times range from about 6 to about 24 hours. Typically, the reaction time for step (a) is from about 12 to about 18 hours.

When the step (a) reaction is complete, the solvent is removed by distillation at atmospheric or reduced pressure, to leave the compound of formula (III) as a residue, which can be used without further purification in subsequent reactions, or can be purified by column chromatography, or by other appropriate means known to the skilled artisan.

Step (b)

Step (b) of the invention process is disclosed in U.S. Pat. No. 6,476,235. In step (b), the ester or amide moiety in the compound of formula (III) is converted in a solvent to an acid moiety in compound (IV) under basic conditions. Thus, for example, the ester is dissolved in aqueous methanol tetrahydrofuran, or the like, and is treated with KOH. Alternatively, the ester can be dissolved in aqueous THF or a non water miscible solvent such as dichloromethane and phase transfer catalyst. Such methods and conditions are known and readily available to the skilled artisan.

Step (c)

Step (c) of the invention process is disclosed in U.S. Pat. No. 6,476,235 and provides 1, which is a convenient precursor to atorvastatin. Lactonization of compound (IV) in step (c) of the invention process occurs in the presence of aqueous acid to provide key intermediate (I). Thus, for example, the acid is stirred in toluene in the presence of a catalytic amount of HCl.

EXAMPLES

The following examples are intended to illustrate various embodiments of the invention and are not intended to restrict the scope thereof.

Example 1

Preparation of (3R,5R)-7-[2-(4-fluorophenyl)-5-isopropyl-3-phenyl-4-phenylcarbamoyl-pyrrol-1-yl]-3,5-dihydroxy-heptanoic acid, t-butyl ester (VI-A)

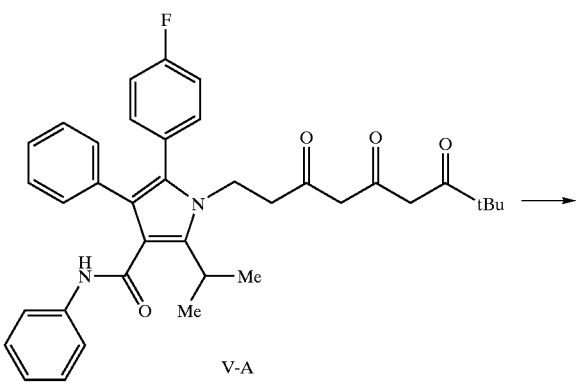

V-A

-continued

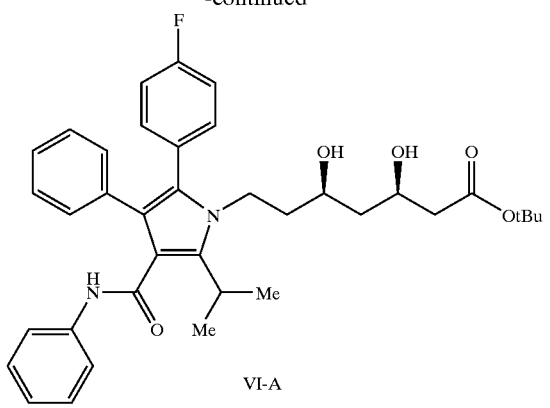

VI-A

An argon inerted reactor was charged with 7-[2-(4-fluorophenyl)-5-isopropyl-3-phenyl-4-phenylcarbamoyl-pyrrol-1-yl]-3,5-dioxo-heptanoic acid, t-butyl ester (V-A, 100.0 mmol, prepared as indicated in U.S. Pat. No. 6,476,235) and toluene (245 ml). To the reaction mixture was added triethyl amine (55 ml), followed by slow addition of formic acid (7.5 ml). The vessel and its contents was degassed via three vacuum/argon purges. Under a steady flow of argon, the complex of Ruthenium, [N-[(1R,2R)-2-(amino-κN)-1,2-diphenylethyl]-4-methylbenzenesulfonamidato-κN]chloro[(1,2,3,4,5,6-η)-1,3,5-trimethylbenzene]-(1.25 g) was added, and the vessel and its contents were degassed via one vacuum/argon purge. The reaction mixture was stirred for 24 hours and condensed to a foamy solid. The crude (3R,5R)-7-[2-(4-fluorophenyl)-5-isopropyl-3-phenyl-4-phenylcarbamoyl-pyrrol-1-yl]-3,5-dihydroxy-heptanoic acid, t-butyl ester may be carried on through subsequent steps without purification, or optionally, can be isolated via flash column chromatography on silica gel, eluting with ethyl acetate-heptane mixtures. HPLC analysis (YMC ODS AQ S5; 1 ml/min; 30° C.; 254 nm: CH$_3$CN/H$_2$O w/0.1% formic acid, 60:40 (0–5 min) to 100:0 (15–22 min) to 60:40 (25 min) indicated a syn:anti ratio of 6:1 t$_r$(syn)=13.9 min t$_r$(anti)=13.5 min Example 2

(3R,5R)-7-[2-(4-fluorophenyl)-5-isopropyl-3-phenyl-4-phenylcarbamoyl-pyrrol-1-yl]-3,5-dihydroxy-heptanoic acid (IV)

The crude (3R,5R)-7-[2-(4-fluorophenyl)-5-isopropyl-3-phenyl-4-phenylcarbamoyl-pyrrol-1-yl]-3,5dihydroxy-heptanoic acid, t-butyl ester (VI-A) was converted to the acid using an excess of KOH/MeOH/Water, followed by lactonization in toluene with catalytic HCl. Chiral HPLC analysis (ChiralCel OF; 1 ml/min; 60° C.; 254 nm; 20% IPA:Hexanes) t$_R$(3R,5R)=26.97 min./t$_R$(3S,5S)=33.8 min. t$_R$(3R,5S)=38.1 min./t$_R$(3S,5R)=61.0 min.) indicated an enantiomeric excess of the syn isomer of 85%, favoring the (R,R) configuration.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for the preparation of a compound of formula (I)

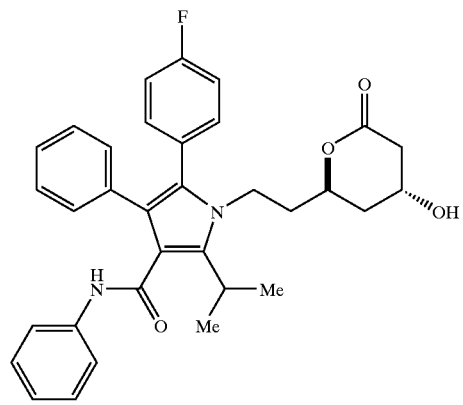

comprising:

(a) contacting in a solvent a compound of formula (II) with a transition metal catalyst, a hydrogen source, and a base wherein the base is selected from the group consisting of NaOH and an anune base, to give a compound of formula (III):

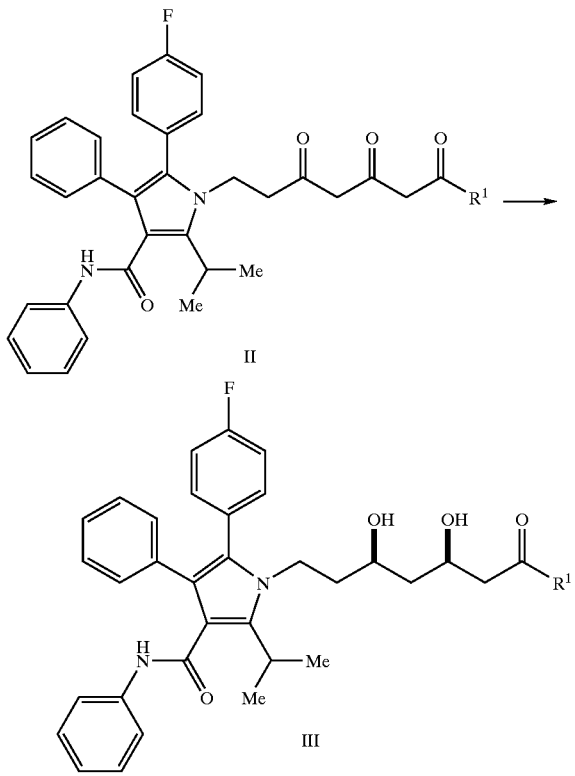

wherein
R$^1$ is defined as —XR, wherein X is O, S, or Se, or

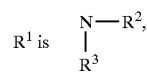

wherein R² and R³ are independently alkyl,
cycloalkyl,
arylalkyl, or
aryl, or
R² and R³ taken together are —(CH₂)₄—,
—(CH₂)₅—,
—(CH(R⁴)—CH₂)₃—,
—(CH(R⁴)—CH₂)₄—,
—(CH(R⁴)—(CH₂)₂—CH(R⁴))—,
—(CH(R⁴)—(CH₂)₃—CH(R⁴))—,
—CH₂—CH₂—A—CH₂—CH₂—,
—CH(R⁴)—CH₂—A—CH₂CH₂—,
—CH(R⁴)—CH₂—A—CH₂—CH(R⁴)—,
   wherein R⁴ is alkyl of from one to four carbon atoms, A is O, S, or N and R is defined as alkyl, aryl, arylalkyl, or heteroaryl;
(b) conversion of the compound of formula (III) wherein R¹ is as defined above to a compound of formula (IV) using base in aqueous methanol or aqueous THF;

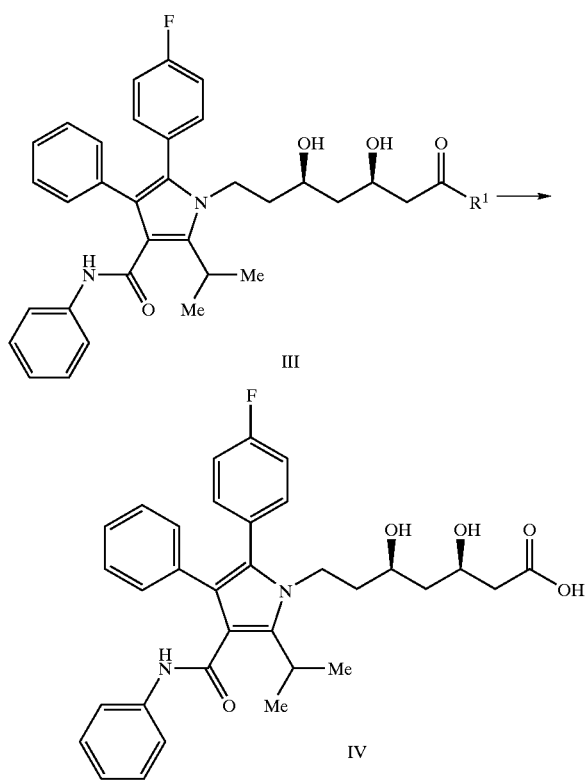

and
(c) contacting in a solvent the compound of formula (IV) with an acid to afford a compound of Formula (I).

2. The process of claim 1, wherein contacting in step (a) comprises mixing the compound of formula I, formic acid, base, and transition metal catalyst in a solvent to form a homogeneous or heterogeneous mixture.

3. The process of claim 2, wherein the solvent in step (a) is an aqueous or anhydrous polar aprotic polar protic, or nonpolar solvent, a ketone, pentane, or hexane, or mixtures thereof.

4. The process of claim 2, wherein the solvent in step (a) is selected from tetrahydrofuran, dimethyl formamide, diethyl ether, methylene chloride, chloroform, methanol, ethanol, isopropanol, and toluene, acetonitrile, ethyl acetate, water, or mixtures or combinations thereof.

5. The process of claim 1, wherein in the compound of formula II or III, R¹ is defined as —XR, wherein X is O and R is alkyl,
cycloalkyl,
arylalkyl,
aryl, or
heteroaryl.

6. The process of claim 1, wherein in the compound of formula II or III, R¹ is defined as —XR, wherein X is O and R is alkyl.

7. The process of claim 1, wherein in the compound of formula II or III, R¹ is OMe, OEt, or Ot—Bu.

8. The process of claim 1, wherein the transition metal catalyst in step (a) is derived from Ir, Ru, or Rh.

9. The process of claim 1, wherein the hydrogen source in step (a) is formic acid, ammonium formate, or isopropanol.

10. The process of claim 1, wherein the hydrogen source in step (a) is formic acid or ammonium formate.

11. The process of claim 1, wherein the hydrogen source in step (a) is formic acid.

12. The process of claim 1, wherein the base in step (a) is an amine base selected from triethylamine, trimethylamine, ethyldimethylamine, tri-n-propylamine, diisopropylethylamine, 1,8-diazabicyclo[5.4.0.]undec-7-ene (DBU), lutidine, collidine, 4-dimethylaminomethyl pyridine, diisopropyl amine, tri-n-butyl amine, 4-methylmorpholine, piperidine, and pyrrolidine.

13. The process of claim 1, wherein the concentration of the compound of formula (II) in the solvent in step (a) is about 0.2 Molar to about 0.6 Molar.

14. The process of claim 1, wherein the concentration of the compound of formula (II) in the solvent in step (a) is about 0.3 Molar to about 0.5 Molar.

15. The process of claim 1, wherein the concentration of the compound of formula (II) in the solvent in step (a) in the solvent is about 0.35 Molar to about 0.45 Molar.

16. The process of claim 1, wherein in step (a), the molar equivalents of each of the compound of formula (II) used is about 1; of the hydrogen source, the base, and the transition metal catalyst are:
   about 1 equivalent of the compound of formula (II);
   about 2.0 to about 2.5 equivalents of hydrogen source;
   about 4.0 to about 5.0 equivalents of amine base; and
   about 0.05 to about 2 mol percent of the transition metal catalyst.

17. The process of claim 1, wherein in step (a), the molar equivalents of each of the compound of formula (II) used is about 1; of the hydrogen source, the base, and the transition metal catalyst are:
   about 1 equivalent of the compound of formula (II);
   about 2.1 to about 2.4 equivalents of hydrogen source;
   about 4.1 to about 4.8 equivalents of amine base; and
   about 1 mol percent of the transition metal catalyst.

18. The process of claim 1, wherein the reaction temperature in step (a) is about 0 to about 50° C.

19. The process of claim 1, wherein the reaction temperature in step (a) is about 10 to about 40° C.

20. The process of claim 1, wherein the reaction temperature in step (a) is about 20 to about 30° C.

21. The process of claim 1, wherein the reaction pressure of step (a) is about 0.9 to about 1.1 atmospheres.

22. The process of claim 1, wherein the reaction pressure of step (a) is about 0.95 to about 1.05 atmospheres.

23. The process of claim 1, wherein the reaction pressure of step (a) is about 0.99 to about 1.02 atmospheres.

24. The process of claim 1, wherein the reaction time of step (a) is about 6 to about 24 hours.

25. The process of claim 1, wherein the reaction time of step (a) is about 12 to about 18 hours.

26. The process of claim 1 wherein the base used in step (b) is KOH.

27. The process of claim 1 wherein the acid used in step (c) is aqueous HCl.

* * * * *